United States Patent [19]

Ser et al.

[11] Patent Number: 4,615,633
[45] Date of Patent: Oct. 7, 1986

[54] PHARMACEUTICAL OR COSMETIC COMPOSITION IN THE FORM OF A ROD OR STICK CONSTITUTED FROM TWO CONCENTRIC FATTY PHASES AND A CASTING PERMITTING ITS PRESERVATION AND DISTRIBUTION

[75] Inventors: Jean-Claude Ser, Chevilly Larue; Jean-Pierre Laugier, Antony, both of France

[73] Assignee: Societe Anonyme dite: L'Oreal, Paris, France

[21] Appl. No.: 668,958

[22] Filed: Nov. 7, 1984

[30] Foreign Application Priority Data

Nov. 9, 1983 [LU] Luxembourg ............................ 85083

[51] Int. Cl.$^4$ .............................................. B05C 21/00
[52] U.S. Cl. .................................... 401/196; 132/88.5
[58] Field of Search ........................ 401/199; 514/569

[56] References Cited

U.S. PATENT DOCUMENTS 3,058,144 10/1962 Schotsch ........................ 401/198 X
3,463,597 8/1969 Wakai ............................ 401/198 X
4,325,179 4/1982 Werwa ................................ 401/199

FOREIGN PATENT DOCUMENTS 39655 3/1961 Luxembourg .
1185173 3/1970 United Kingdom .

Primary Examiner—Gregory E. McNeill
Attorney, Agent, or Firm—Cushman, Darby & Cushman

[57] ABSTRACT

A rod or stick for pharmaceutical or cosmetic use in topical application to the skin of an easily oxidizable active substance comprises an internal fatty phase or core phase containing in an anhydrous medium the oxidizable active substance. The said core phase is protected from oxidation by an external fatty phase or sheath phase containing at least one surface active agent. The said sheath phase entirely envelopes the circumferential surface and at least one end section of said core phase.

11 Claims, 1 Drawing Figure

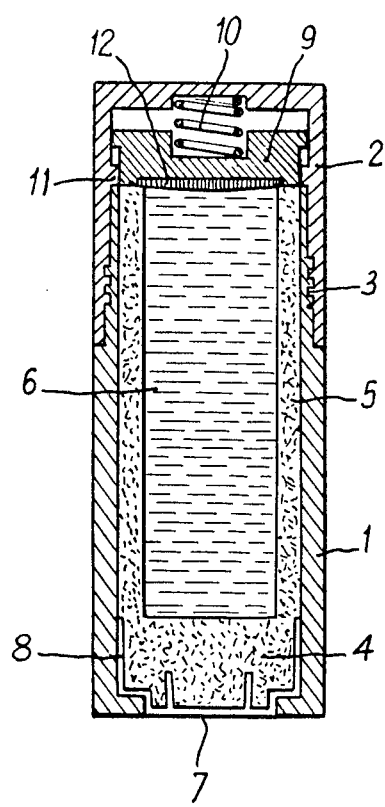

PHARMACEUTICAL OR COSMETIC COMPOSITION IN THE FORM OF A ROD OR STICK CONSTITUTED FROM TWO CONCENTRIC FATTY PHASES AND A CASTING PERMITTING ITS PRESERVATION AND DISTRIBUTION

The present invention relates to a new form of packaging easily oxidizable active substances provided in the form of a rod or stick and comprising two concentric fatty phases, and a case so as to permit is preservation and distribution.

Various substances which are particularly sensitive to oxidation by the oxygen of the air are employed therapeutically in dermatologic treatments. Representative ones of such substances include particularly, anthralin or dithranol and their derivatives, idoxuridine, tretinoin and the like.

These substances, as well as others, although having been known to be particularly active in their respective therapeutic capabilities have not, however, always been found to enjoy wide spread use or acceptance.

This is particularly true with regard to anthralin or dithranol which have been shown to be very active in the treatment of psoriasis.

Anthralin is a substance which is very easily degraded by oxidation into quinones or into polymeric products, having a deep color and being capable of staining the skin and clothing.

Moreover, anthralin, as well as its oxidation products are particularly irritating which thus has limited its use in the treatment of psoriasis.

Various forms of compositions have, however, already been proposed with the view of the packaging and administrating application to the skin of easily oxidizable substances such as anthralin.

These compositions, even if they provide substantial improvement in preserving the anthralin, they are however not always practical in use especially when, in the treatment of psoriasis, the active substances must be applied only on the affected portions of the skin and not come into contact with healthy areas of the skin which would then cause undesirable irritation of these unaffected areas of skin.

Consequently, when compositions are provided in the viscous form produced, for example, from paraffin and zinc oxide or from a mixture of paraffin and petrolatum, such compositions produce a discharge which reaches or comes into contact with areas of the skin other than those which are to be treated.

Moreover, these compositions due to the nature of the vehicle or carrier most often are based on petrolatum and are therefore quite difficult to remove once applied to the skin.

The present invention overcomes the disadvantages of known compositions containing easily oxidizable products and principally compositions based on anthralin or its derivatives by formulating such substances in the shape of a rod or stick, thus permitting precise local application thereof to the areas of the skin to be treated. The present invention, due to its composition and structure, also provides the advantages of avoiding oxidation of the active substance and of facilitating removal of the composition from the skin after treatment.

The present invention thus relates to, as a new industrial product, a rod or stick, for cosmetic or pharmaceutical use, for the optical application to the skin of an easily oxidizable substance, this rod or stick comprising a first internal fatty phase or "core" phase containing in an anhydrous medium the said oxidizable active substance, the said "core" phase being protected from oxidation by a second external fatty phase or "sheath" phase containing at least one surfactant, the said "sheath" phase being disposed around and on at least one of the end sections of the said "core" phases.

The presence of the external fatty phase, enveloping the internal fatty phase containing the easily oxidizable active substance, avoids any contact of the latter with the atmosphere, thus preventing or at least considerably retarding the degradation of the easily oxidizable substances by the oxygen of the air. This structural feature thus preserves the rod or stick for long periods of time after its initial use.

After its first use, the stick, which initially is covered by a variable thickness of the protective external fatty phase or by any other means, can be protected from oxidation by various means and more particularly with the aid of certain closure devices of the casing for the stick, said casing being provided with an element adaptable to the application surface of the stick. This element is capable of receiving a fatty phase identical or similar in its composition to that of the external fatty phase of the stick.

This aspect of the invention, relative to the distribution and preservation of the stick according to the invention is described hereafter in reference to the particular mode of fabrication.

According to the present invention, the easily oxidizable active substance which can be soluble in the internal fatty phase or core, must be only slightly soluble or insoluble in the external fatty phase or sheath.

In order to assure a relatively uniform and simultaneous wearing out of the two phases the liquefaction temperature of the external fatty phase must not differ more than about 20° C. from the liquefaction temperature of the internal fatty phase. The liquefaction temperature of the external phase ranges from 40° to 80° C., it being understood that the liquefaction temperature of the internal phase should not be lower than about 40° C.

The external fatty phase is generally made from paraffinic waxes, micro-crystalline waxes (waxes having paraffinic chains branched by rings) or by other waxes such as, principally, ozokerite, carnauba wax, candellila wax and by paraffin oils of various viscosities.

In addition this external fatty phase can contain silicone oils such as, for example, alkylpolysiloxanes, aryl polysiloxanes, hydrogenated lanolins optionally modified such as ethoxylated, acetylated or esterified lanolins, polymers such as vinyl acetate/allyl stearate polymers (described in French Pat. No. 2.232.303), polyvinyl laurate polymers, poly butene polymers and polyisobutene polymers.

The surface active agent present in the external fatty phase or "sheath" phase must be soluble in the fatty body and must exhibit, alone or combined with at least one other surface active agent, a gross HLB (Griffin) value of 6 to 12 and preferably 8 to 10.

The concentration of the surfactant in this phase can vary from 5 and 30 weight percent relative to the total weight of the external fatty phase.

Representative surface active agents include
(1) nonionic surfactants having an HLB of 4–14 such as:
  (a) ethoxylated alcohols, for example those known under the commercial designation of "BRIJ 30", sold by Atlas, (b) ethoxylated alkyl-aryl, for example, the product known under the commercial tradename of "LUBROL N 5" sold by ICI, (c) esters of sugar or sorbitan, optionally ethoxylated, for example, the product known under the commercial names of "SPAN 20" or "TWEEN 65" sold by Atlas, as well as (2) anionic surfactants having an acid function, and having an HLB of 4–6 such as (d) alkyl surfonics or alkyl-aryl sulfonics and (e) phosphoric esters, for example those known under the commercial name of "HOSTAPHAT KL 240", sold by Hoechst.

The presence of at least one non-ionic or anionic surfactant in the external phase permits easy removal of the composition from the skin without it being necessary to employ a rinsing composition which is generally acidic in nature. By applying of a sufficient amount of water, once the treatment time has elapsed, the surface active agent permits complete removal of the composition from the portions of the skin previously treated.

The internal fatty phase which constitutes the fatty support for the active substance, is prepared in such a manner that its liquifaction temperature assures in satisfying manner, the deposit of the active substance, and it is generally carried out using various fatty bodies in the presence, optionally, of a viscosity agent and/or a non-ionic surfactant so as to facilitate the dispersion and the solubilization of the active substance therein.

Representative fatty bodies include the mono-, di- and tri-esters of glycerol wherein the saturated fatty acid radicals have 8 to 20 carbon atoms and are of natural origin (for example hydrogenated vegetable oils) or semi-synthetic origin such as products known under the commercial names of "WITEPSOL", "SOFTISAN", "MIGLYOL" and the like sold by Dynamit Nobel, fatty esters having 8–40 carbon atoms, linear or branched, having a melting temperature lower than 70° C., fatty alcohols, having preferably 12–18 carbon atoms, fatty acids, having preferably 8–16 carbon atoms, paraffinic waxes, microcrystalline waxes, ozokerite, carnauba wax, candellila wax, paraffin oils of various viscosity grades, silicone oils, polyether oligomers, principally the dimethyl ether of polytetrahydrofuran, saturated solvents such as the polyethers or the ethers-/esters described in French Pat. Nos. 2.222.351 and 2.281.743 and in particular the products of the formulas

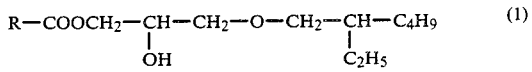

wherein
R represents $C_{21}H_{43}$ or $C_{15}H_{31}$ and

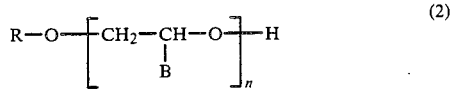

wherein
R is a 2-hexyldecyl or 2-ethylhexyl radical,
n is 2 or 6 and

B represents $C_{10}H_{21}$ or $-CH_2OR'$ wherein R' is a $C_{12}H_{25}/C_{14}H_{29}$ mixture.

Representative optional viscosity agents incorporated into the internal fatty phase include, the triglycerides of hydrogenated ricin oil, such as the product known under the commercial name of "THIXCINR" sold by NL Industries, colloidal silicas, such as those known under the commercial name of "AEROSIL R 972" sold by Degussa, glycol esters, in particular diesters such as ethylene glycol distearate and principally that known under the commercial name of "SYNCHROWAX ERLC" sold by Croda or α-diol ether/esters such as laurylglycol palmitate.

As the optional surfactants there are preferably employed non-ionic surfactants having a saturated liposoluble fatty chain, and having an HLB lower than 4, which assists in the dispersion and solubilization of the active substance.

Representative ones of these optional surfactants include, principally, sorbitan esters or glycerol esters such as: "SPAN 65" (sorbitan tristearate) or "ATMOS 150" (glycerol mono- and di-stearate) sold by Atlas and those described in French Pat. Nos. 1.477.048, 2.091.516 and 2.465.780 and in particular compounds of the formulas:

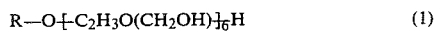 (1)

wherein R represents a $C_{16}H_{33}/C_{18}H_{37}$ mixture,

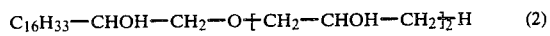 (2)

and

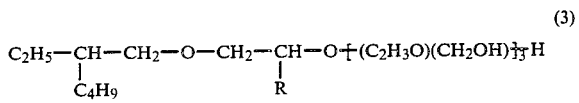 (3)

wherein R represents $C_{16}H_{33}$ or $-CH_2-O_{16}H_{33}$.

The internal fatty phase, as well as the external fatty phase, of the rod or stick according to the present invention can also contain other components, principally anti-oxidant agents which increase stability against oxidation. Representative anti-oxidants include butylhydroxyanisol, butylhydroxytoluene, and gallates such as propyl gallate.

The two fatty phases can also contain salicylic acid in an amount from 0.01 to 5 percent by weight relative to the weight of each of the phases.

The amount of the active substance in the internal fatty phase can vary as a function of the active substance to be administered, but the amount is generally between 0.01 and 5 percent by weight based on the total weight of this internal phase.

The rod or stick according to the present invention is generally obtained by separately preparing the internal fatty phase or core and the external fatty phase or sheath and then successively molding them.

In accordance with the invention one can mold, indifferently, initially either the external fatty phase or the internal fatty phase. However, in accordance with a preferred embodiment, the external fatty phase is initially molded in an appropriate mold containing an internal sleeve which is removed after cooling and hardening the thus molded external phase. Thereafter the composition comprising the internal fatty phase which contains the oxidizable active substance, is poured into the cavity created by the removed sleeve. The upper section or surface of the resulting stick is then covered by a layer of external fatty phase, so as to preserve it before its use.

The process of molding must permit a melting-mixing at the level of the junction of the two fatty phases so as to assure good cohesion of the rod or stick according to the invention.

The thickness of the external fatty phase can vary and depends on the relative hardness of the two phases so as to obtain a stick which exhibits long lasting characteristics and which is capable of facilitating good spreadability of the stick. The thickness of this external phase is generally not greater than the radius of the internal fatty phase.

It goes without saying that the preparation of the rod or stick according to the invention should, if possible, be carried out in the absence of air and under a gaseous inert atmosphere, for example, nitrogen.

The size as well as the form of the sticks can vary, the diameter generally being between 5 and 50 mm and the form preferably being cylindrical, although other forms having a symmetrical axis are also envisaged, for example, a stick or rod in hexagonal form.

Other characteristics and advantages will be evident from the following descriptions which is given as an example and from the drawing which represents a cross-sectional view of a casing and its closure arrangement for the rod or stick in accordance with the present invention.

In the drawing (1) is the body of a casing for the stick whose closure cap (2) is fitted thereon by a screw fastening arrangement (3).

At the interior of the casing (1) is housed a stick (4) in accordance with the invention said stick comprising an external fatty phase or sheath (5) and an internal fatty phase or core (6).

At the base of the casing an opening (7) is provided so that the user can push the stick or rod outside of the casing when open with his finger, the base of the stick being molded in a housing (8) and being in frictional engagement with the interior of the body of the casing (1).

In this embodiment, the frictional engagement between the stick or rod and the internal walls of the body of the casing (1) is such that the stick does not freely return to its initial position.

The closure cap (2) which is fitted onto the body by a screw fastening arrangement carries a movable part or piston (9) capable of being displaced axially of the body along the length of the internal wall of the cap (2) between its upper surface and annular flange (11), disposed at the internal periphery of the cap (2) and receiving support on the flanges of the body (1) of the casing when it is in the closed position.

In its position of rest, the piston (9) is located on the annular flange (11) under the effect of an elastic means represented in the drawing in the form of a spring (10).

The lower portion of the piston (9) has a generally convex surface, said piston being manufactured from a single block, and preferably is provided with a cavity (12) which is capable of receiving a fatty composition identical or similar to the external fatty phase of the stick made in accordance with the present invention.

The closure system represented in the drawing assures excellent preservation of the stick against oxidation.

After its use, the stick (4) will slightly project beyond the upper edge of the body (1). By screwing of the cap (2) onto the casing the piston (9) exerts pressure on the stick (4) and again completely covers the upper surface thereby assuring complete protection of the stick from oxidation by the oxygen of the air Although the present invention has been described in reference to a particular embodiment, it is obvious that changes and modifications can be made without departing from the scope and spirit of the invention. In particular, the advancement of the stick to a position outside the casing body can be achieved using other systems, for example, conventional screw means which are commonly employed in association with numerous cosmetic products and which retains the stick in such a given position that it does not freely return to its initial position. The spring (10) associated with the piston (9) can also be replaced by any other means such as compressed air, which imparts an elastic effect.

The following non-limiting examples are given to illustrate the present invention.

EXAMPLE 1

Into a rod or stick mold having an internal diameter of 35 mm and a length of 70 mm and fitted in the central portion thereof with a removable sleeve having a diameter of 15 mm and a length of 65 mm, there is poured at a temperature of 60° C. a sufficient amount of an external fatty phase or sheath obtained by admixing the following components:

| | |
|---|---|
| Paraffin wax | 24% |
| Viscous petrolatum | 52% |
| Paraffin oil | 12% |
| Phosphate of lauryl alcohol oxyethylenated with 4 moles of ethylene oxide, sold under the tradename "HOSTAPHAT KL 240" | 6% |
| Sorbitan laurate, sold under the tradename "SPAN 20" | 6% |
| | 100% |

After cooling and hardening the external phase the sleeve is removed and into the cavity thus created there is poured at a temperature of 42° C. a sufficient amount of an internal phase or core obtained by admixing the following components:

| | |
|---|---|
| Semi-synthetic triglycerides having 12–16 carbon atoms and sold under the tradename "SOFTISAN 100" | 67% |
| Stearyl alcohol | 15% |
| Cetyl alcohol | 15.45% |
| Butyl hydroxyanisole + Butyl hydroxy toluene | 0.05% |
| Salicylic acid | 1% |
| Anthralin | 1.5% |

After cooling the internal phase the stick is unmolded and placed in an appropriate casing of corresponding diameter. The external fatty phase of the stick has a liquefaction temperature of 58° C. and the internal fatty phase has a liquefaction temperature of 40° C.

EXAMPLE 2

In accordance with the procedures described in Example 1 and using a mold having the same characteristics, a stick is prepared using the following external and internal phases:

| External phase | |
|---|---|
| Ozokerite | 19% |
| Paraffin oil | 20% |
| Viscous petrolatum | 39% |
| Ethoxylated alcohol, sold under the tradename "BRIJ 30" | 22% |
| | 100% |
| Internal phase | |
| Paraffin wax | 20% |
| Viscous petrolatum | 54% |
| Paraffin oil | 23.95% |
| Salicylic acid | 1% |
| Butyl hydroxytoluene | 0.05% |
| Anthralin | 1% |

The external fatty phase of the stick thus obtained has a liquefaction temperature of 52° C. and the internal fatty phase has a liquefaction temperature of 48° C.

What is claimed is:

1. A rod or stick for pharmaceutical or cosmetic use in the topical application to the skin of an easily oxidizable active substance comprises a first internal fatty phase or core phase containing in an anhydrous medium said oxidizable active substance, the said core phase being protected from oxidation by a second external fatty phase or sheath phase containing at least one surface active agent, the said sheath phase entirely enveloping the circumferential surface and at least one end section of said core phase.

2. The rod or stick of claim 1 wherein the external fatty phase has a liquefaction temperature which does not differ more than 20° C. from that of the internal fatty phase, the liquefaction temperature of the external fatty phase being between 40° and 80° C. and the liquefaction temperature of the internal fatty phase being not greater than 40° C.

3. The rod or stick of claim 1 wherein the surface active agent of the said external fatty phase has a total HLB (Griffin) value of 6 to 12, said surface active agent being a non-ionic or anionic surface active agent.

4. The rod or stick of claim 3 wherein said external fatty phase has an HLB of 8 to 10.

5. The rod or stick of claim 3 wherein the concentration of the surface active agent is between 5 and 30 weight percent based on the total weight of said external fatty phase.

6. The rod or stick of claim 1 wherein said internal fatty phase contains one or more of one or both of a viscosity agent and a non-ionic surface active agent.

7. The rod or stick of claim 1 wherein the said external and internal fatty phases contain an antioxidant.

8. The rod or stick of claim 7 wherein said antioxidant is selected from butylhydroxyanisole, butylhydroxytoluene or propyl gallate.

9. The rod or stick of claim 1 wherein one or both of said internal or external fatty phases also contains salicylic acid in an amount from 0.01 to 5 percent by weight based on the weight of the fatty phase in which it is incorporated.

10. The rod or stick of claim 1 wherein said active substance is present in an amount from 0.01 to 5 weight percent based on the total weight of the internal fatty phase.

11. The rod or stick of claim 1 wherein said active substance is anthralin or dithranol or a derivative thereof, or idoxuridine, or tretinoin.

* * * * *